United States Patent [19]

Szeles

[11] Patent Number: 5,324,287
[45] Date of Patent: Jun. 28, 1994

[54] NEEDLE AND THERAPEUTIC DEVICE FOR STIMULATING SPECIFIC POINTS OF THE BODY

[76] Inventor: Josef C. Szeles, Glanzinggasse 5/7, A-1190 Vienna, Austria

[21] Appl. No.: 688,571
[22] PCT Filed: Nov. 21, 1989
[86] PCT No.: PCT/AT89/00107
 § 371 Date: Jul. 16, 1991
 § 102(e) Date: Jul. 16, 1991
[87] PCT Pub. No.: WO90/05560
 PCT Pub. Date: May 31, 1990

[30] Foreign Application Priority Data

Nov. 21, 1988 [AT] Austria ................. 2846/88
Nov. 21, 1988 [AT] Austria ................. 2850/88

[51] Int. Cl.$^5$ ............................................. A61B 17/34
[52] U.S. Cl. ................................ 606/41; 606/189; 411/411
[58] Field of Search ................. 606/189, 204, 41; 411/411

[56] References Cited

U.S. PATENT DOCUMENTS

| 3,939,841 | 2/1976 | Dohring et al. |
| 4,244,375 | 1/1981 | Farrar et al. ............ 128/642 |
| 4,262,672 | 4/1981 | Kief .......................... 606/189 |

FOREIGN PATENT DOCUMENTS

| 150525 | 4/1937 | Austria . |
| 379079 | 11/1985 | Austria . |
| 0229200 | 7/1987 | European Pat. Off. . |
| 80051 | 7/1894 | Fed. Rep. of Germany . |
| 319602 | 8/1914 | Fed. Rep. of Germany . |
| 3437493A1 | 4/1986 | Fed. Rep. of Germany . |
| 969374 | 12/1950 | France . |
| 1297117 | 5/1962 | France . |
| 2345994 | 10/1977 | France . |
| 2392650 | 12/1978 | France . |
| 7618557 | 3/1979 | France . |
| 239028 | 9/1945 | Switzerland . |
| 620821 | 12/1980 | Switzerland . |
| 957917 | 9/1982 | U.S.S.R. . |
| 1296164 | 3/1987 | U.S.S.R. ................. 606/189 |
| 1296164 | 3/1987 | U.S.S.R. . |
| 1514079 | 6/1978 | United Kingdom . |

OTHER PUBLICATIONS

International Search Report dated Mar. 20, '90.
Austrian Office Action Dated Apr. 19, '89 for Appl. A2846/88.
Austrian Office Action Dated Apr. 20, '89 for Appl. A2850/88.

*Primary Examiner*—Michael H. Thaler
*Attorney, Agent, or Firm*—Collard & Roe

[57] ABSTRACT

The puncturing stimulation needle has an insertion part (2) and a holder part (3). The insertion part (2) is structured as a screw with one or more threads, the thread height (6) of which is greater than twice the diameter (7) of the insertion part (2) at its thickest point. Preferably, the holder part (3) is structured in the form of a ring or small disk, with its side facing the insertion part (2) lying in a plane approximately perpendicular to the geometric axis of the insertion part. The puncturing stimulation therapy apparatus has a portable, battery-powered treatment current generator (17), with at least one electrode (23, 24) in the form of a puncturing stimulation needle being connected with the generator via a flexible line (21, 22), with this needle having an insertion part (2) which is shorter than 4 mm, and a holder part (3) in the form of a ring or small disk. A surface electrode (29) can also be provided at the housing of the treatment current generator (17).

18 Claims, 2 Drawing Sheets

FIG. 6
FIG. 7
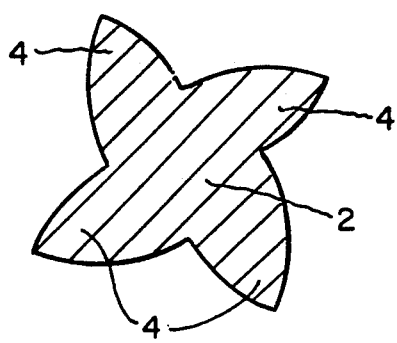
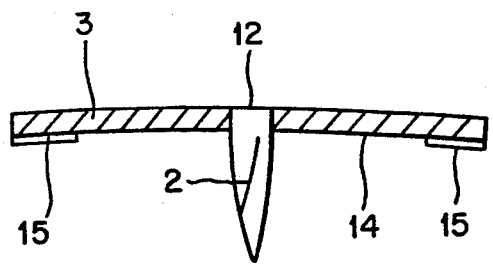
FIG. 8
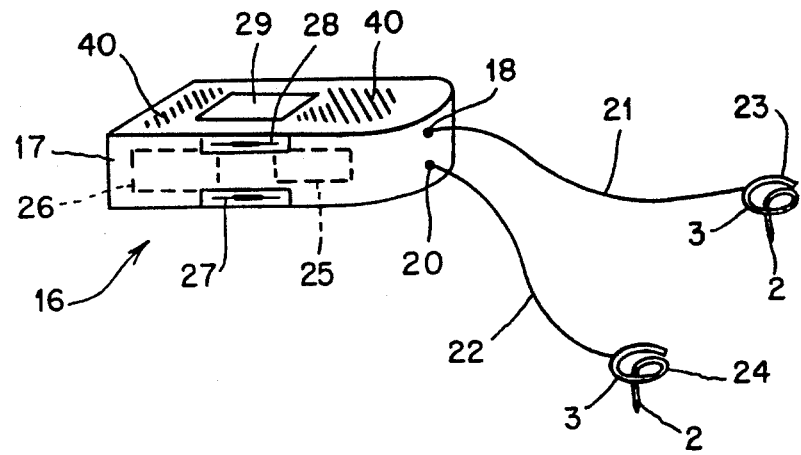
FIG. 9
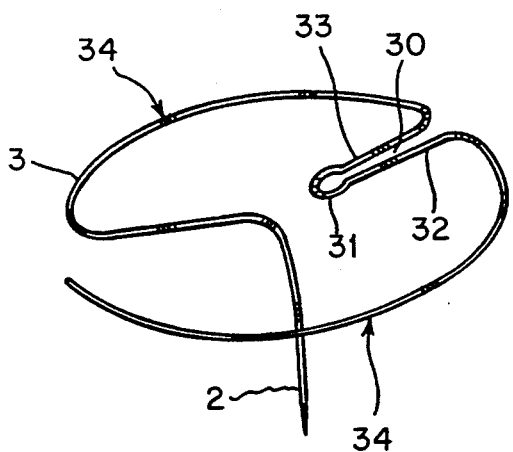
FIG. 10
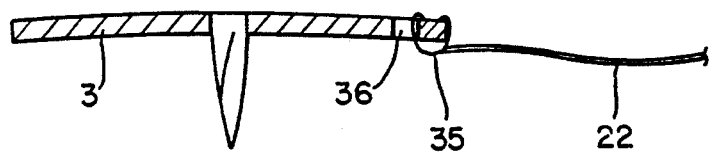

NEEDLE AND THERAPEUTIC DEVICE FOR STIMULATING SPECIFIC POINTS OF THE BODY

BACKGROUND OF THE INVENTION

1. Field of the Invention

The invention related to a puncturing stimulation needle with an insertion part in the form of a straight pin, uniformly narrowing towards the tip, and a holder part.

The invention furthermore relates to a puncturing stimulation therapy apparatus with a portable, battery-powered treatment current generator and with electrodes which are connected to this treatment current generator.

2. The prior Art

At a number of sites in the body, there are receptor regions located below the skin surface, which have a stimulus-conduction connection with body parts located at other sites of the body. By stimulating such receptor regions, influence can be exerted on the body parts which are in connection with these receptor regions, for diagnostic or therapeutic purposes. Puncturing stimulation needles serve the purpose of bringing about a stimulation of the receptor regions which are located at the body surface, i.e. in the skin, and have a stimulus-conduction connection with certain body parts, in order to influence the body parts assigned to these sites, by inserting the needles into the receptor regions. Such an effect is also the goal of acupuncture.

The stimulation needles generally used for acupuncture have an insertion part, which has a smooth surface and in which the region immediately following the tip has a diameter of approximately 0.25 mm. This insertion part generally has a length of about 10 to 15 mm, and is followed by a holder part, which is usually of an approximately cylindrical shape and has a diameter of about 2 to 3 mm.

For the determination of assignments between receptor regions and body parts, and also for the stimulation of receptor regions by the insertion of puncturing stimulation needles, it is of significant importance that the puncturing stimulation needles be inserted as accurately as possible at those sites where the receptor regions are located. It is furthermore important that the puncturing stimulation needles have a good hold, as soon as they are inserted at the correct location, so that the desired effect is maintained for an extended period of time. Both requirements are only insufficiently fulfilled with the aforementioned needles usually used in acupuncture. In order to give the needles with a smooth insertion part a sufficiently stable hold in the skin, these needles are generally inserted so deeply that such a hold of the needles is guaranteed, with this insertion depth often being clearly greater than the depth at which the receptor regions to be stimulated are located, and such relatively deep insertion of the needles is often felt to be unpleasant; the feeling of a pin prick is superimposed on the stimulation effect and can reduce this effect. Furthermore, when inserting such needles, the penetration resistance also often becomes detrimentally obvious, with the result that shifts occur during insertion, with a detrimental effect on exactly reaching the receptor regions.

It can be mentioned that electrodes are known from DE-A-28 23 307 which are intended for insertion into the skin and are supposed to serve for a determination of electrophysiological voltages (ECG). The known electrodes consist of a pin pointed at one end, intended for insertion into the skin, which has one or more bulb-type bulges, and of an approximately cylindrical base part, in which the pin is attached. Precisely targeted insertion of these electrodes under the skin is detrimentally affected by the said bulges. An embodiment with a bulge twisted like a screw is also shown.

SUMMARY OF THE INVENTION

It is the goal of the present invention to create a puncturing stimulation needle which allows easy and sensitively controlled penetration of the insertion part into the skin, and which simultaneously makes it possible to achieve a secure hold at the insertion site, even at a slight insertion depth. The puncturing stimulation needle according to the invention, of the type mentioned initially, is characterized by the fact that the insertion part is structured as a screw with one or more threads, the thread height of which is greater than twice the diameter of the insertion part at its thickest point, and that preferably, the holder part is structured in the form of a ring or small disk, with its side facing the insertion part lying in a plane approximately perpendicular to the geometric axis of the insertion part. With this structure, the goal stated above can be fulfilled very well. The screw-shaped structure of the insertion part allows sensitive introduction of the needle tip into the skin, by application of a slight rotating movement, and the penetration depth can also be controlled well, and furthermore, because of the screw shape of the insertion part of the needle, a good hold of the needle is achieved even with a relatively slight insertion depth. The structure of the holder part of the needle which is preferably provided, in the shape of a ring or small disk, makes it possible to easily recognize the extent of rotation when inserting and removing the needle, and furthermore allows a good support of the needle on the skin area surrounding the insertion point to be achieved, which advantageously contributes to a secure hold of the needle. Because of the structure of the holder part, the needle can furthermore be additionally fixed in place with an adhesive strip covering the holder part, so that an exact hold of the needle is guaranteed over extended periods of time and simultaneously, the insertion site is protected against contamination, to a great extent.

In many cases, an embodiment which is characterized by the fact that the screw which forms the insertion part has approximately ¼ to ½ thread has proven to be advantageous.

It is advantageous if the length of the insertion part of the needle is chosen to be less than 4 mm, for most cases of use. For stimulation of receptor regions located on the body, it is advantageous if the length of the insertion part of the needle is chosen to be approximately 3 mm. For auricular stimulation, a length of the insertion part of about 1 to 2 mm is advantageous, where it is advantageous if the length of the needles intended for insertion into cartilage area of the ear is selected to be about 1 mm, while for insertion into other parts of the ear, a length of the insertion part of about 2 mm is advantageous.

In order to further improve the support and hold effect of the holder part of the puncturing stimulation needle, it is advantageous if an adhesive is provided on the side of the holder part which comes to rest on the skin, which can be structured, for example, in the form of an adhesive layer or in the form of a ring of a self-adhesive film.

In order to achieve the smoothest possible insertion of the needle, it is advantageous if the screw thread has a sharp thread ridge on the outside. With such a structure, in combination with sensitive handling, the discomfort often felt upon insertion can be reduced to a minimum. At the same time, it is also advantageous if the thread screw has a flat groove directly following the thread ridge, seen in the cross-section of the profile.

Stimulation of receptor regions by the introduction of electric currents has already been attempted, and for this purpose, electrodes which rest on the skin surface have generally been used. This technique is sometimes called "electric acupuncture." A stimulation therapy apparatus designed for this technique is known, which has a very small, battery-powered treatment current generator, which can be easily worn on the body due to its small size, and which is connected with an electrode carrier via flexible lines, this carrier having several pin electrodes which are rounded off at their front side, and which is placed on the part of the body to be treated. A significant disadvantage of this apparatus and, in general, of electric acupuncture, which uses electrodes placed on the skin surface, is that this type of electric acupuncture is often able to achieve only a very slight effect, and sometimes no noticeable effect at all can be achieved with such treatment.

Also with a device known from FR-A-969 374, in which a glove acting as the carrier has several electrodes attached at the tips of the glove fingers, and a multi-lead flexible cable is provided to connect these electrodes with a treatment current source, contacting of the skin surface with the electrodes takes place; among other things, an electrode form is provided in which a cone-shaped tip is arranged in the center of a frontal surface of a cylinder-like element.

It was found that direct puncturing stimulation of the receptor regions is able to yield a good therapeutic effect in almost all cases. However, it is hardly possible for a patient to wear the long stimulation needles generally used in acupuncture for an extended period of time, since the position of these needles, i.e. their hold and insertion depth, can be altered in undesirable manner by outside forces. Furthermore, the stimulation effect of such needles often decreases significantly after some time.

It is now a further goal of the present invention to create a puncturing stimulation therapy apparatus with which stimulation of receptor regions can be undertaken over extended periods of time, in a practically achievable manner.

The invention creates a puncturing stimulation therapy apparatus of the type mentioned initially, which is characterized by the fact that at least one electrode is a puncturing stimulation needle connected with the treatment current generator via a flexible line, the insertion part of which is shorter than 4 mm, and which has a holder part, immediately following the insertion part, in the form of a ring or small disk, with its side facing the insertion part lying in a plane approximately perpendicular to the geometric axis of the insertion part, and that preferably, a surface electrode is provided at the housing of the treatment current generator. With this structure, the goal stated above can be fulfilled very well. Because of the fact that at least one electrode of the apparatus is a puncturing stimulation needle connected with the treatment current generator via a flexible line, a current which causes stimulation can be introduced directly into a receptor region, and since the treatment current generator can be easily worn on the body, the stimulation can also be undertaken over extended periods of time; the special structure of the puncturing stimulation needle which is provided for the puncturing stimulation therapy apparatus according to the invention allows simple handling when placing the needle, and also makes it possible to achieve secure hold of the needle over extended periods of time, resistant to moderate forces acting from the outside, since the holder part of the needle is well supported against the skin area surrounding the insertion point, and since the needle can be easily protected, in addition, with an adhesive strip covering it.

This apparatus is especially well suited for auricular therapy, in which the puncturing stimulation needle forming the electrode is inserted into receptor regions on the external ear.

A preferred embodiment of the puncturing stimulation therapy apparatus according to the invention is characterized by the fact that the insertion part of the electrode(s) is structured as a screw with one or more threads, the thread height of which is greater than twice the diameter of the insertion part of the needle at its thickest point. For one thing, this embodiment allows particularly sensitive and precise insertion of the electrode or electrodes, which facilitates reaching the receptor regions, and extensively alleviates the discomfort usually felt upon insertion of needles into the skin, and for another, a further improvement of the hold of the electrode at the insertion point is achieved with this structure of the insertion part of the electrode.

It is advantageous if the length of the insertion part of the puncturing stimulation needle forming the electrode(s) is chosen to be less approximately 3 mm, for stimulation of receptor regions located on the body, i.e. on the torso or extremities. For auricular therapy, a length of the insertion part of about 1 to 2 mm is advantageous, where it is advantageous if the length of the electrodes intended for insertion into cartilage areas of the ear is selected to be about 1 mm, while for insertion into other parts of the ear, a length of the insertion part of about 2 mm is advantageous.

In order to further improve the support and hold effect of the holder part of the puncturing stimulation needle(s) forming the electrode(s), it is advantageous if an adhesive is provided on the side of the holder part which comes to rest on the skin, which can be structured, for example, in the form of an adhesive layer or in the form of a ring of a self-adhesive film.

It is also advantageous to undertake adhesive fixation of the flexible line(s) to the electrode(s) on the skin. For this purpose also, an adhesive layer can be provided on the line(s), or a thin self-adhesive film can be provided on the line(s).

Particularly smooth introduction or insertion of the insertion part of the electrode, almost completely avoiding unpleasant sensations, can be achieved with an embodiment of the puncturing stimulation therapy apparatus according to the invention which is characterized by the fact that the screw thread has a sharp thread ridge on the outside.

If the insertion part of the electrode or the electrodes is structured as a screw, it is advantageous, in many cases, to have the greatest possible thread height, e.g. a thread height which results in approximately $\frac{1}{4}$ to $\frac{1}{2}$ thread over the length of the insertion part of the needle.

With regard to the needle, both from the point of view of its manufacture and from the point of view of its manipulation, an embodiment of the puncturing stimulation therapy apparatus according to the invention which is characterized by the fact that the holder part is a ring bent from wire, with one end of this wire being bent away radially to the ring center, and proceeding from there, being bent once again to form the insertion part, is very advantageous.

Because of the introduction of stimulation into the receptor regions themselves, by means of a puncturing stimulation needle, the stimulation with the puncturing stimulation therapy apparatus according to the invention is sufficient at very low current levels, generally just a few microamperes; to achieve this, the impulse generator to be provided in the apparatus only has to give off relatively low output, and accordingly, it can be operated from a relatively small battery over extended periods of time. In this way, relatively small overall dimensions of the treatment current generator can be achieved, so that the latter can be worn at any desired part of the body, e.g. directly behind the ear. The surface electrode provided at the housing of the treatment current generator in a preferred embodiment of the puncturing stimulation therapy apparatus can be connected with a pole of the output of the treatment current generator, so that for stimulation, only a needle electrode has to be used; however, it is also possible, if desired, to use several electrodes in the form of puncturing stimulation needles, which are structured as explained above, and to connect both output terminals of the treatment current generator with acupuncture needles.

The puncturing stimulation therapy apparatus according to the invention can also be structured as a disposable apparatus, in view of its simple structure, which is particularly advantageous for hygienic reasons.

To hold the treatment current generator in place on the body, e.g. behind the ear, a molded attachment piece or an adhesive strip can be provided. It is also advantageous to provide an adhesive on the outside of the housing of the treatment current generator.

BRIEF DESCRIPTION OF THE DRAWINGS

The invention is now explained in greater detail with reference to examples which are shown in the drawings. In the drawing, FIG. 6 shows a further variation of the insertion part in a cross-sectional representation corresponding to FIG. 3 and 5, and FIG. 7 shows a further embodiment of a puncturing stimulation structured according to the invention in a cross-sectional representation;

FIG. 8 shows an embodiment of a puncturing stimulation therapy apparatus according to the invention in a projection, FIG. 9 shows an electrode with an integrated connector clamp, and FIG. 10 shows an electrode connected with a line via a connector clamp.

DETAILED DESCRIPTION OF THE PREFERRED EMBODIMENTS

Figure 1:
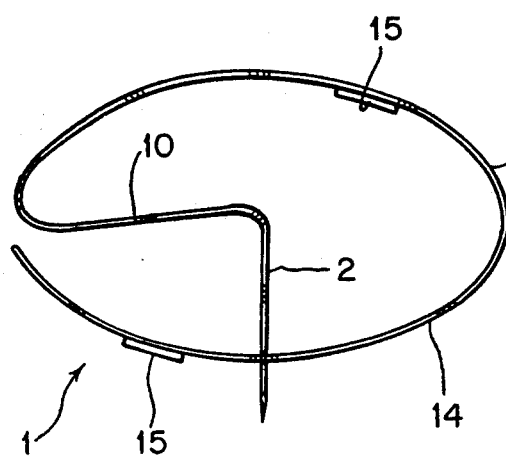
FIG. 1 shows a first embodiment of a puncturing stimulation needle structured according to the invention in a projection.
Figure 2:
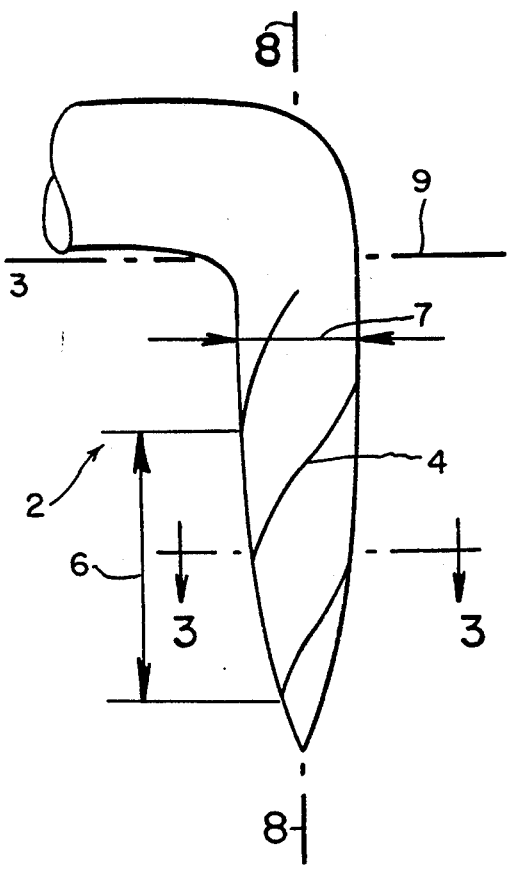
FIG. 2 shows the insertion part of such a needle, also in projection, on an enlarged scale as compared with FIG. 1.
Figure 3:
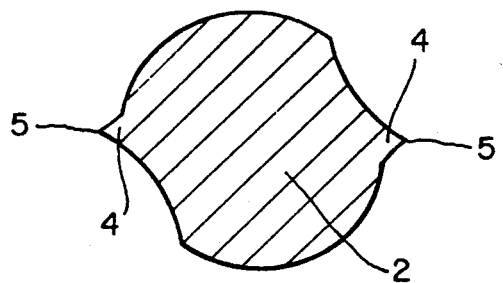
FIG. 3 shows a cross-section along the line III—III in FIG. 2, on a more enlarged scale.

The embodiment of a puncturing stimulation needle 1 shown in FIG. 1 to 3 has an insertion part 2 and a holder part 3. The insertion part 2 is structured as a two-thread screw, with the screw thread 4 having sharp thread ridges 5 on the outside. The thread height 6 of the screw thread 4 is greater than twice the diameter 7 &hat the insertion part has at its thickest point. The screw thread 4 has a shallow profile, as is directly evident from FIG. 3.

The holder part 3 is structured in the form of a ring, with its side facing the insertion part lying in a plane 9 approximately perpendicular to the geometric axis 8 of the insertion part 2. The holder part 3 is bent from wire, with one end 10 of this wire being bent away radially to the ring center, and proceeding from there being bent once again to form the insertion part 2.

The length of the insertion part 2 is approximately 2 mm in this embodiment, and the diameter of the ring 3 is approximately 4 mm. The thickness 7 of the insertion part is approximately 0.3 mm.

Figure 5:
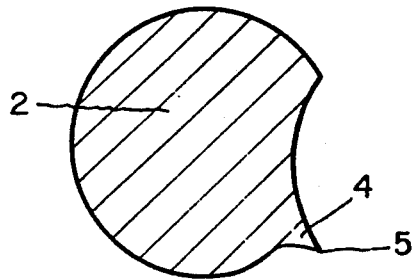
FIG. 5 shows a cross-section along the line V—V in FIG. 4 in a more enlarged scale.
Figure 4:
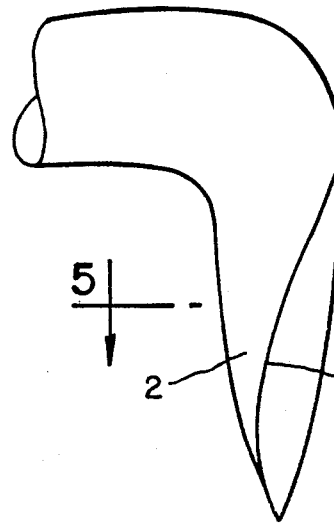
FIG. 4 shows a variation of the insertion part of such a needle in a representation corresponding to FIG. 2.

In the variation shown in FIG. 4 and 5, the insertion part 2 is structured in the form of a one-thread screw, with the screw thread again, as FIG. 5 shows, having a sharp thread ridge 5, and a shallow profile. The screw which forms the insertion part 2 has ½ thread in this case. The length of the insertion part is approximately 1 mm in this case.

In the variation shown in FIG. 6, the insertion part 2 is structured as a four-thread screw, with the screw thread 4 having a greater profile depth than in the embodiments shown in FIG. 3 and 5.

In the embodiment according to FIG. 7, the holder part 3 is structured in the form of a small disk, which is connected with the insertion part 2 at its center 12. The insertion part 2 can be placed into a corresponding opening in the small disk, with a positive or non-positive lock, or can be connected with the small disk with a solder or weld bond, for example. The structure of the insertion part can also be in a different way here, as is shown in FIG. 2 to 6, for example.

On the side 14 of the holder part 3 which comes to rest against the skin, an adhesive 15, for example in the form of an adhesive layer or in the form of a ring of self-adhesive film, can be arranged.

The puncturing stimulation therapy apparatus 16 shown schematically in FIG. 8 has a treatment current generator 17, with electrodes 23, 24 attached to its output terminals 18, 20 via flexible lines 21, 22. In the housing of the treatment current generator 17, an electrical impulse generator, i.e. function generator 25 is arranged, which generates the treatment currents and, if desire, is structured so that it can be switched with regard to impulse form or wave form, impulse frequency or wave frequency, as well as with regard to impulse intervals. This impulse generator or function generator is supplied from a battery 26 inserted into the housing of the treatment current generator 17. A switch 27 is provided to turn the impulse generator on and off. Another switch 28 serves to switch on a surface electrode 29 provided at the housing of the treatment current generator 17, to one of the output terminals 18, 20 of the treatment current generator 17.

The electrodes 23, 24 are puncturing stimulation needles, the insertion part 2 of which is shorter than 4 mm, and which have a holder part 3 immediately following the insertion part 2, which is structured in the form of a ring or small disk. In many practical cases, e.g. in auricular therapy, a length of the insertion part of about 1 mm to 2 mm can be provided. The side of the holder part 3, structured as a ring or small disk, which faces the insertion part 2, lies in a plane which is approximately perpendicular to the geometric axis 8 of the insertion part 2, as indicated with the dot-dash line 9 in FIG. 2. With this structure of the holder part of the punctual stimulation needle which forms an electrode, good support of a needle inserted into a skin site on the skin area surrounding the insertion point is achieved, which contributes advantageously to a secure hold of the needle. With this structure of the holder part, the needle can also be further fixed in place using an adhesive strip which covers the holder part, so that a precise hold of the needle is guaranteed over extended periods of time, and simultaneously, the insertion point is protected against contamination, to a great extent.

In the embodiment shown in FIG. 8, as with the needle according to FIG. 1 to 4, the holder part 3 is a ring bent from wire, with one end of the wire being bent away radially to the ring center, and proceeding from there, being bent away once again to form the insertion part 2.

It is advantageous if the electrodes 23, 24 are structured in the form of the needles shown in FIG. 1 to 7.

The electrodes structured in the form of a special puncturing stimulation needle can be soldered or welded to the flexible line 21, 22 coming from the treatment current generator to form an electrical connection, in the simplest case, or such a line can be connected with the electrode in question by means of a clamp connector. A clamp connector can, if desired, also be structured so that it can be released, so that if desired, different electrodes, which differ with regard to the length of the insertion part, for example, can be used. FIG. 9 shows an embodiment of an electrode which is structured similar to the electrode or needle shown in FIG. 1, and a connector clamp 30 integrated into the holder part. To form this connector clamp 30, the ring which forms the holder part 3 is provided with a U-shaped indentation 31, the shanks 32, 33 of which can be spread open in the direction of the arrows 34 by compressing the ring; in this way, the clamp 30 can be opened and the end of an electrical line can be introduced between the shanks 32, 33, which then spring back, after the force which opens the clamp is released again, and hold the electrical line in place.

A connector clamp 35 can also be provided at a flexible line 21, 22 leading to an electrode, to create an electrical connection between the line in question and the electrode structured as a puncturing stimulation needle, using this connector clamp. Such an embodiment is shown in FIG. 10. The connector clamp 35, attached to a flexible line 22, which is structured in the form of an elastic ring, engages over the edge of a holder part 3 of the electrode in question, structured as a small disk in this case, with its one side, and engages through an opening 36 provided in this holder part 3 with its other shank, and in this way, a very secure hold of the flexible line 22 on the holder part 3 of the electrode is achieved.

For stimulation with the puncturing stimulation therapy apparatus, a current conducted over two electrodes, which are structured in the manner explained above, in the form of special puncturing stimulation needles, can be used; as shown in FIG. 1, the two electrodes are connected to the output terminals of the treatment current generator 17, which have different polarity. If desired, a larger number of electrodes, which are connected with the treatment current generator 17 via flexible lines, can also be used with this type of stimulation. Such a line can also carry several electrodes, in series behind one another, if necessary. In many cases it is advantageous to connect a surface electrode 29 to one pole of the stimulation current circuit which is supplied from the treatment current generator, and to connect one or more electrode(s) structured as (a) puncturing stimulation needle(s) to the other pole of this current circuit. However, if desired puncturing stimulation needle electrodes can also be connected to both output terminals of the treatment current generator, and a surface electrode can be connected, in addition, to one of the output terminals; here the switch 28 can be structured in such a way that the surface electrode 29 can be optionally connected with one of the two output terminals of the treatment current generator 17, using the switch.

In addition to the surface electrode, an adhesive 40 to hold the treatment current generator in place on the body can be provided.

What is claimed is:

1. A puncturing stimulation therapy apparatus comprising:
    a portable battery powered current source and electrodes electrically coupled to said current source;
    a flexible cable electrically coupled to said current source;
    a puncturing stimulation needle electrically coupled to said flexible cable, said puncturing stimulation needle including
    i. an insertion part having a longitudinal axis and a screw thread with a distance between two corresponding points of said screw thread along the length of said insertion part that is greater than twice the largest diameter of said insertion part, said screw thread having an exterior and a sharp thread ridge on the exterior, said insertion part having a length less than 4 mm; and
    ii. a ring-shaped holder part attached to said insertion part and lying in a plane approximately perpendicular to the longitudinal axis of said insertion part.

2. The puncturing stimulation therapy apparatus according to claim 1, additionally including a housing for containing said current source, said housing including a surface electrode.

3. The puncturing stimulation therapy apparatus according to claim 1, wherein said screw thread winds around said insertion part approximately one quarter to one half of its circumference.

4. The puncturing stimulation therapy apparatus according to claim 3, additionally including a housing for containing said current source, said housing including a surface electrode.

5. The puncturing stimulation therapy apparatus according to claim 1, wherein the length of said insertion part is less than 2 mm.

6. The puncturing stimulation therapy apparatus according to claim 5, wherein the length of said insertion part is about 1 mm.

7. The puncturing stimulation therapy apparatus according to claim 6, additionally including a housing for containing said current source, said housing including a surface electrode.

8. The puncturing stimulation therapy apparatus according to claim 1, wherein said puncturing stimulation needle is made from a wire, said wire forming said ring-shaped holder part and having
   i. a first bend directing said wire radically inward towards the longitudinal axis and
   ii. a second bend directing said wire along the longitudinal axis to form said insertion part.

9. The puncturing stimulation therapy apparatus according to claim 8, additionally including a housing for containing said current source, said housing including a surface electrode.

10. The puncturing stimulation therapy apparatus according to claim 1, wherein said flexible cable includes an adhesive.

11. The puncturing stimulation therapy apparatus according to claim 10, additionally including a housing for containing said current source, said housing including a surface electrode.

12. The puncturing stimulation therapy apparatus according to claim 1, additionally including a housing to contain said current source, said housing having an adhesive layer.

13. The puncturing stimulation therapy apparatus according to claim 12, wherein said housing includes a surface electrode.

14. A puncturing stimulation needle comprising:
   an insertion part formed as a straight pin and having a longitudinal axis with a first end, a second tip end, and a diameter that narrows continuously from said first end along the length of said straight pin towards said second tip end, said insertion part having a screw thread with a distance between two corresponding points of said screw thread along the length of said insertion part that is greater than twice the largest diameter of said straight pin, said screw thread having an exterior and a sharp thread ridge on the exterior, said screw thread is formed as a shallow groove adjacent to said sharp thread ridge; and
   a holder part attached to said first end of said straight pin.

15. The puncturing stimulation needle according to claim 14, wherein said holder part is ring-shaped and lies in a plane disposed approximately perpendicular to the longitudinal axis of said insertion part.

16. The puncturing stimulation needle according to claim 15, wherein said holder part has a lower side facing, said second tip end and includes an adhesive on said lower side for adhering said holder part to a skin surface.

17. A puncturing stimulation therapy apparatus comprising:
   a portable battery powered current source and electrodes electrically coupled to said current source;
   a flexible cable electrically coupled to said current source;
   a puncturing stimulation needle electrically coupled to said flexible cable, said puncturing stimulation needle including:
   i. an insertion part having a longitudinal axis and a screw thread with a distance between two corresponding points of said screw thread along the length of said insertion part that is greater than twice the largest diameter of said insertion part, said screw thread having an exterior and a sharp thread ridge on the exterior, said insertion part having a length less than 4 mm;
   ii. a ring shaped holder part having a lower side and attached to said insertion part and lying in a plane approximately perpendicular to the longitudinal axis of said insertion part; and
   iii. an adhesive disposed on said lower side of said ring shaped holder part for adhering said holder part to a skin surface.

18. The puncturing stimulation therapy apparatus according to claim 17, additionally including a housing for containing said current source, said housing including a surface electrode.

* * * * *